US010888564B2

(12) United States Patent  
Andrake et al.

(10) Patent No.: US 10,888,564 B2  
(45) Date of Patent: Jan. 12, 2021

(54) INHIBITORS OF HIV-1 INTEGRASE MULTIMERIZATION

(71) Applicant: Institute for Cancer Research, Philadelphia, PA (US)

(72) Inventors: Mark D. Andrake, Philadelphia, PA (US); Anna Marie Skalka, Philadelphia, PA (US); George W. Merkel, Philadelphia, PA (US)

(73) Assignee: Institute for Cancer Research, Philadelphia, PA (US)

( * ) Notice: Subject to any disclaimer, the term of this patent is extended or adjusted under 35 U.S.C. 154(b) by 0 days.

(21) Appl. No.: 16/480,624

(22) PCT Filed: Jan. 26, 2018

(86) PCT No.: PCT/US2018/015502  
§ 371 (c)(1),  
(2) Date: Jul. 24, 2019

(87) PCT Pub. No.: WO2018/140762  
PCT Pub. Date: Aug. 2, 2018

(65) Prior Publication Data  
US 2019/0381054 A1 Dec. 19, 2019

Related U.S. Application Data

(60) Provisional application No. 62/450,846, filed on Jan. 26, 2017, provisional application No. 62/526,605, filed on Jun. 29, 2017.

(51) Int. Cl.  
*A61K 31/4245* (2006.01)  
*A61K 31/454* (2006.01)  
*A61K 31/53* (2006.01)

(52) U.S. Cl.  
CPC .......... *A61K 31/53* (2013.01); *A61K 31/4245* (2013.01); *A61K 31/454* (2013.01)

(58) Field of Classification Search  
CPC ... A61K 31/53; A61K 31/4245; A61K 31/454  
See application file for complete search history.

(56) References Cited

U.S. PATENT DOCUMENTS

2005/0282818 A1 12/2005 Ramesh et al.  
2008/0032984 A1 2/2008 Petry et al.  
2013/0280271 A1 10/2013 Skalka et al.

FOREIGN PATENT DOCUMENTS

WO 2012088513 6/2012

OTHER PUBLICATIONS

Andrake et al., "Multimerization determinants reside in both the catalytic core and C terminus of avian sarcoma virus integrase" J Biol Chem, 1995, 270, pp. 29299-29306.

(Continued)

*Primary Examiner* — Marcos L Sznaidman  
*Assistant Examiner* — Rayna Rodriguez  
(74) *Attorney, Agent, or Firm* — Stradley Ronon Stevens & Young, LLP

(57) ABSTRACT

The disclosure generally relates to compounds of formulas (I) and (II)7 including compositions and methods for treating human immunodeficiency virus (HIV) infection. The disclosure provides novel inhibitors of HIV-1 integrase, pharmaceutical compositions containing such compounds, and methods for using these compounds in the treatment of HIV infection.

8 Claims, 4 Drawing Sheets

(56) References Cited

OTHER PUBLICATIONS

Bao et al., "Functional oligomeric state of avian sarcoma virus integrase" J Biol Chem, 2003, 278, pp. 1323-1327.

Bojja et al., "Architecture and assembly of HIV integrase multimers in the absence of DNA substrates", J Biol Chem, 2013, 288, pp. 7373-7386.

Deprez et al., "Oligomeric states of the HIV-1 integrase as measured by time-resolved fluorescence anisotropy" Biochemistry, 2000, 39, pp. 9275-9284.

Engelman et al., "Identification of discrete functional domains of HIV-1 integrase and their organization within an active multimeric complex", EMBO J, 1993, 12, pp. 3269-3275.

Engelman et al., "Retroviral intasomes arising", Curr Opin Struct Biol, 2017, 47, pp. 23-29.

Faure et al., "HIV-1 integrase crosslinked oligomers are active in vitro", Nucleic Acids Res, 2005, 33(3), pp. 977-986.

Feng et al., "The A128T resistance mutation reveals aberrant protein multimerization as the primary mechanism of action of allosteric HIV-1 integrase inhibitors", J Biol Chem, 2013, 288, pp. 15813-15820.

Hare et al., "Retroviral intasome assembly and inhibition of DNA strand transfer", Nature, 2010, 464, pp. 232-236.

International Search Report and Written Opinion dated May 1, 2018 for corresponding International Patent Application No. PCT/US2018/015502.

Jurado et al., "Allosteric integrase inhibitor potency is determined through the inhibition of HIV-1 particle maturation", Proc Natl Acad Sci USA, 2013, 110, pp. 8690-8695.

Korolev et al., "Structural-Functional Analysis of 2,1,3-Benzoxadiazoles and Their N-oxides as HIV-1 Integrase Inhibitors", Acta Nature, 2013, 5(1), pp. 63-72.

Lesbats et al., "Retroviral DNA Integration" Chem Rev, 2016, 116, pp. 12730-12757.

Li et al., "Retroviral DNA integration: reaction pathway and critical intermediates" EMBO J, 2006, 25, pp. 1295-1304.

Nagamatsu et al., "Syntheses of 3-substituted 1-methyl-6-phenylpyrimido[5,4-e]-1,2,4-triazine-5,7(1H,6H)-diones (6-phenyl analogs of toxoflavin) and their 4-oxides, and evaluation of antimicrobial activity of toxoflavins and their analogs", Chem Pharm Bull, 1993, 41(2), pp. 362-368.

Third Party Observation dated May 27, 2019 submitted in corresponding International Patent Application No. PCT/US2018/015502.

Zheng et al., "Zinc folds the N-terminal domain of HIV-1 integrase, promotes multimerization, and enhances catalytic activity" Proc Natl Acad Sci USA., 1996, 93, pp. 13659-13664.

Zufferey et al., "Self-inactivating lentivirus vector for safe and efficient in vivo gene delivery", J Virol, 1998, 72, pp. 9873-9880.

INHIBITORS OF HIV-1 INTEGRASE MULTIMERIZATION

CROSS-REFERENCE TO RELATED APPLICATIONS

This application is a U.S. National Phase filing of international patent application number PCT/US2018/015502, filed Jan. 26, 2018, that claims priority under 35 U.S.C. § 119(e) to U.S. provisional patent application No. 62/526,605, filed on Jun. 29, 2017 and U.S. provisional patent application No. 62/450,846, filed on Jan. 26, 2017, the entireties of which are incorporated herein by reference.

STATEMENT OF GOVERNMENT SUPPORT

The inventions described herein were made, in part, with funds obtained from the National Institutes of Health, Grant Nos. AI-040385 and AI-118589. The U.S. government may have certain rights in these inventions.

FIELD OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

BACKGROUND OF THE INVENTION

Various publications, including patents, published applications, technical articles and scholarly articles are cited throughout the specification. Each of these cited publications is incorporated by reference herein, in its entirety and for all purposes.

HIV infection remains a major world health issue requiring ongoing research to design new methods to treat the disease and to combat the spread of the virus. Integrase (IN) is a virus-encoded enzyme that catalyzes the insertion of viral DNA into the DNA of the infected host cell. IN is one of three retrovirus-encoded enzymes that are essential for retroviral replication and is an established target for the development of drugs to treat HIV/AIDS.

Recognizing the efficacy of targeting this viral enzyme, the FDA has approved three IN active-site inhibitors, Raltegravir, Elvitegravir, and Dolutegravir. Nevertheless, drug-resistant HIV mutants that are cross-resistant to all three inhibitors demonstrate a continuing need for inhibitors that target locations away from the active site by allosteric mechanisms.

For Integrase to function it must form multimers (at least dimers and tetramers, see FIG. 1A models) and perform a coordinated insertion of two viral DNA ends into the host target DNA, in a reaction called concerted integration. A partial defective reaction occurs when one viral end is inserted (called single end integration), and this reaction likely reflects impaired Integrase multimerization. To take an alternate approach to the discovery of allosteric inhibitors that target this required Integrase multimerization, we designed a FRET-based assay to detect reaching dimer formation (see FIG. 1B), and used it to screen the 50,000 compound chemical diversity library of ChemDiv, ltd. at 10 uM concentration.

Retroviral IN proteins are composed of three distinct structural domains (for review see, e.g., Lesbats, P., Engelman, A. N., Cherepanov, P. Retroviral DNA Integration. Chem Rev 116:12730-12757, 2016. PMCID: PMC5084067 and the references therein). The largest of these, the central catalytic core domain (CCD or "core"), contains the D,D (35)E motif of acidic residues, which coordinate the required divalent metal ions, Mg+2 or Mn+2. The flanking domains include the Zn+2-binding N terminal (NTD) and the SH3-like C-terminal (CTD) domains.

For proper integrase function, the protein must form multimers competent to perform a coordinated insertion of two viral DNA ends into the host target DNA, called concerted integration. An incomplete reaction in which only one viral end is inserted (single-end integration) presumably occurs as a consequence of impaired integrase multimerization. It is believed that inhibiting proper IN multimerization will be an effective antiviral strategy. Structural models have been obtained of full-length HIV-1 IN dimers in the absence of nucleic acids or accessory proteins using small angle X-ray scattering (SAXS) and protein-protein cross-linking methods (Bojja, R. S., Andrake, M. D., Merkel, G., Weigand, S., Dunbrack, R. L., Jr., Skalka, A. M. Architecture and assembly of HIV integrase multimers in the absence of DNA substrates. J Biol Chem 288:7373-7386, 2013. PMCID: 3591645). The results revealed an unexpected dimer architecture, that is referred to herein as a "reaching dimer", as it is mediated by interactions of the flanking N-terminal and C-terminal domains.

A detailed structural knowledge of the HIV-1 IN assembly and catalysis reveals unexploited vulnerabilities and novel strategies for inhibiting this critical enzyme. Depending on the concentration, full-length IN proteins exist as monomers, dimers, and tetramers in solution (FIG. 1A) (see, Andrake, M. D., Skalka, A. M. Multimerization determinants reside in both the catalytic core and C terminus of avian sarcoma virus integrase. J Biol Chem 270:29299-29306, 1995; Deprez, E., Tauc, P., Leh, H., Mouscadet, J. F., Auclair, C., Brochon, J. C. Oligomeric states of the HIV-1 integrase as measured by time-resolved fluorescence anisotropy. Biochemistry 39:9275-9284, 2000; and Zheng, R., Jenkins, T. M., Craigie, R. Zinc folds the N-terminal domain of HIV-1 integrase, promotes multimerization, and enhances catalytic activity. Proc. Natl. Acad. Sci. U.S.A. 93:13659-13664, 1996), and complementation experiments verify that IN functions as a multimer (Engelman, A., Bushman, F. D., Craigie, R. Identification of discrete functional domains of HIV-1 integrase and their organization within an active multimeric complex. EMBO J. 12:3269-3275, 1993. PMCID: PMC413594). Correspondingly, IN must join two processed viral DNA ends to host DNA in a coordinated fashion in vivo, and a tetramer is the minimal functional multimer for this step (see Bao, K. K., Wang, H., Miller, J. K., Erie, D. A., Skalka, A. M., Wong, I. Functional oligomeric state of avian sarcoma virus integrase. J. Biol. Chem. 278:1323-1327, 2003; Li, M., Mizuuchi, M., Burke, T. R., Jr., Craigie, R. Retroviral DNA integration: reaction pathway and critical intermediates. EMBO J. 25:1295-1304, 2006. PMCID: PMC1422164; and Engelman, A. N., Cherepanov, P. Retroviral intasomes arising. Curr Opin Struct Biol 47:23-29, 2017).

Others have targeted the LEDGF binding site at the CCD dimer interface of HIV-1 IN for inhibition. Designed as allosteric inhibitors, these compounds drive aberrant IN multimerization, cause defects in virus particle maturation, and are effective at inhibiting virus infectivity (Jurado, K. A., Wang, H., Slaughter, A., Feng, L., Kessl, J. J., Koh, Y., Wang, W., Ballandras-Colas, A., Patel, P. A., Fuchs, J. R., Kvaratskhelia, M., Engelman, A. Allosteric integrase inhibitor potency is determined through the inhibition of HIV-1 particle maturation. *Proc Natl Acad Sci USA* 110:8690-8695, 2013). However, resistance to this class of compounds has also been described (Feng, L., Sharma, A., Slaughter, A., Jena, N., Koh, Y., Shkriabai, N., Larue, R. C., Patel, P. A., Mitsuya, H., Kessl, J. J., Engelman, A., Fuchs, J. R., Kvaratskhelia, M. The A128T resistance mutation reveals aberrant protein multimerization as the primary mechanism of action of allosteric HIV-1 integrase inhibitors. *J Biol Chem* 288:15813-15820, 2013), and none have been approved by the FDA for clinical use. Accordingly, in the face of the continuing battle against resistant virus variants, there is an ongoing need to develop inhibitors that have a new mechanism of action.

SUMMARY OF THE INVENTION

Compounds of the present invention target a different dimeric interface than the CCD dimer targeted in the prior art. Specifically, as an alternate approach to the discovery of allosteric inhibitors that target functional integrase multimerization, the present inventors designed a FRET-based assay that specifically detects formation of the reaching dimer, and used it to screen a 50,000 compound chemical diversity library. Compounds disclosed herein were found to inhibit this dimer formation and most fell into two distinct scaffold classes with differential effects on integrase catalytic function and inhibition of infection in cell culture.

In one aspect, the present invention provides a method for inhibiting HIV-1 integrase multimerization in a cell, the method comprising contacting HIV-1 integrase with an amount of a compound effective to inhibit the biologic activity of HIV-1 integrase, wherein the compound is selected from the group consisting of a compound from Formula I and Formula II, wherein Formula I is defined by the structure:

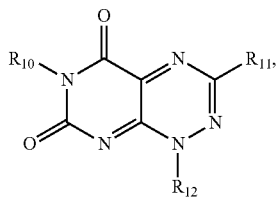

(I)

wherein $R_{10}$ and $R_{12}$ are each independently a H or a $C_1$-$C_3$ alkyl group;

$R_{11}$ is H, a $C_1$-$C_3$ alkyl group,

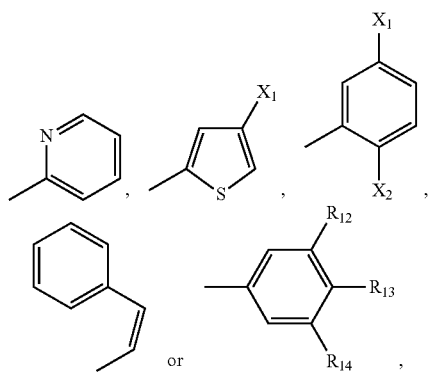

wherein each of $R_{12}$, $R_{13}$, and $R_{14}$ are independently selected from the group consisting of H, a $C_1$-$C_3$ alkyl group, $-NO_2$, halogen, $-CH_2F$, $-CHF_2$, and $-CF_3$, and wherein $X_1$ and $X_2$ are halogens and are either the same or different; and Formula II is defined by the structure:

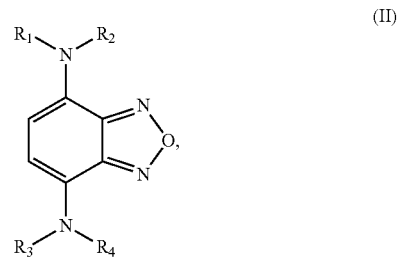

(II)

wherein $R_1$, $R_2$, $R_3$, and $R_4$ are independently selected from a hydrogen atom, an aliphatic group having a carbon number of from 1 to 18 in which one or more hydrogen atoms may be substituted by a halogen atom, an aliphatic group having a carbon number of from 2 to 18 which comprises at least one moiety selected from the group consisting of $-O-$, $-S-$, $-C(=O)-$, $-C(=O)-O-$, $-C(=O)-S-$, $-C(=O)-NH-$, $-N$-succinimidyl, and $-O-C(=O)-NH-$, wherein at least one of the pairs $R_1$ and $R_2$ or $R_3$ and $R_4$ may be connected to form an alicyclic group, and wherein the aliphatic group optionally comprises at least one halogen atom.

In another aspect, the present invention provides a method for treating an HIV patient in need thereof, comprising administering to the patient an effective amount of an HIV-1 integrase multimerization inhibitor selected from the group consisting of a compound from Formula I and Formula II, wherein Formula I is defined by the structure:

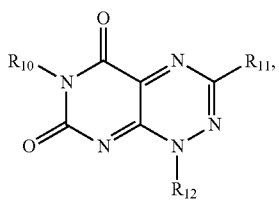

(I)

wherein $R_{10}$ and $R_{12}$ are each independently a H or a $C_1$-$C_3$ alkyl group;

$R_{11}$ is H, a $C_1$-$C_3$ alkyl group,

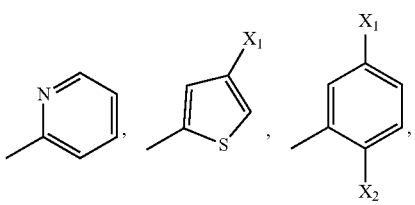

-continued

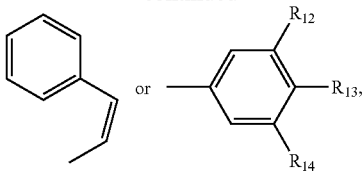

wherein each of $R_{12}$, $R_{13}$, and $R_{14}$ are independently selected from the group consisting of H, a $C_1$-$C_3$ alkyl group, —$NO_2$, halogen, —$CH_2F$, —$CHF_2$, and —$CF_3$, and wherein $X_1$ and $X_2$ are halogens and are either the same or different; and Formula II is defined by the structure:

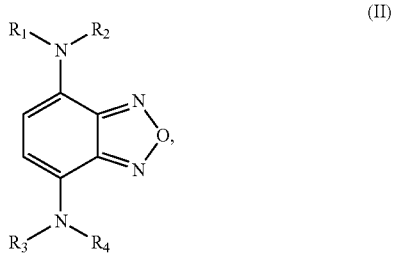

wherein
$R_1$, $R_2$, $R_3$, and $R_4$ are independently selected from
a hydrogen atom,
an aliphatic group having a carbon number of from 1 to 18 in which one or more hydrogen atoms may be substituted by a halogen atom,
an aliphatic group having a carbon number of from 2 to 18 which comprises at least one moiety selected from the group consisting of —O—, —S—, —C(=O)—, —C(=O)—O—, —C(=O)—S—, —C(=O)—NH—, —N-succinimidyl, and —O—C(=O)—NH—,
wherein at least one of the pairs $R_1$ and $R_2$ or $R_3$ and $R_4$ may be connected to form an alicyclic group, and wherein the aliphatic group optionally comprises at least one halogen atom.

BRIEF DESCRIPTION OF THE DRAWINGS

FIG. 1A shows structures for HIV-1 IN monomer and two different dimers that were derived by data-driven modeling, based on small-angle X-ray scattering and protein cross-linking data. The IN substitutions that lead to the predominance of either dimer are shown next to the corresponding arrow. Catalytic core domains (CCDs) are rendered in surface representation to emphasize their locations in the structures, and the helical N-terminal domains (NTDs) are darker, while C-terminal domains (CTDs) appear as white ribbons. The assay described here looked for compounds that inhibit the formation of the reaching dimer shown on the right. FIG. 1B illustrates the HIV-IN (F181T) reaching dimer and design of a FRET donor and acceptor positions for this multimerization assay. This view of the reaching dimer is similar to that shown in 1A on the right, but now one entire monomer is colored white while the other is dark gray. The C280 residues to which the donor and acceptor are covalently attached are shown as large spheres, and connected with a dotted line measuring 33 Å. This distance is sufficiently close to achieve a FRET signal suitable for a robust screening assay.

DETAILED DESCRIPTION OF THE INVENTION

Various terms relating to aspects of the invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Subject and patient are used interchangeably. A subject may be any animal, including mammals such as companion animals, laboratory animals, and non-human primates. Human beings are preferred.

Figure 1A:
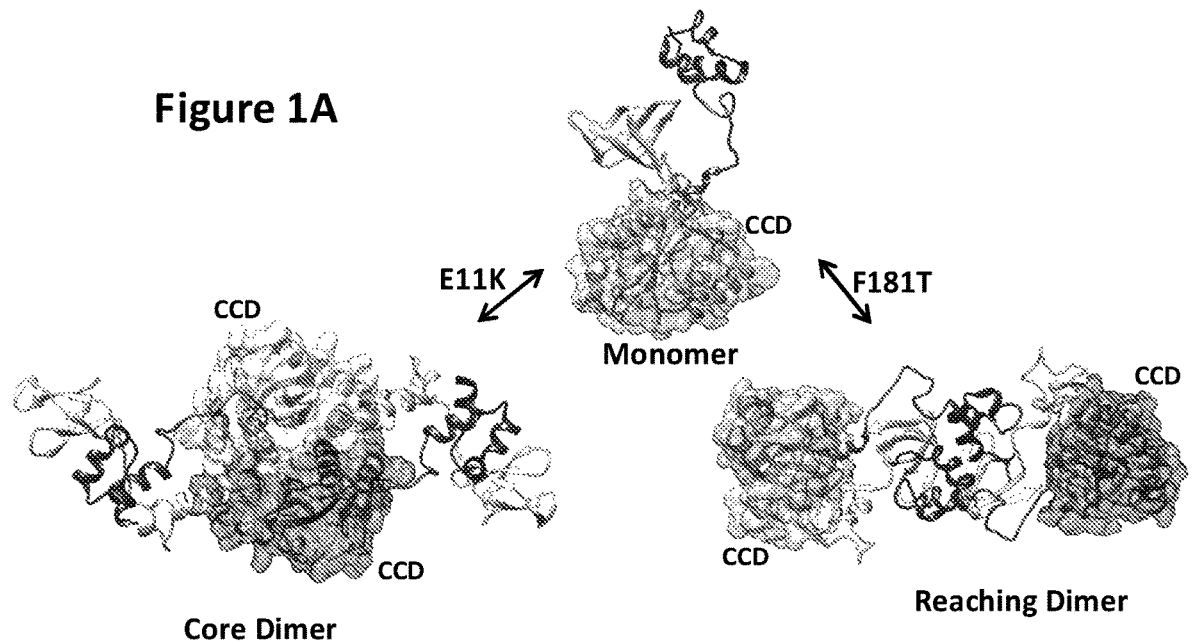
FIGS. 1A and 1B illustrate models of HIV-1 integrase protein in solution.
Figure 1B:
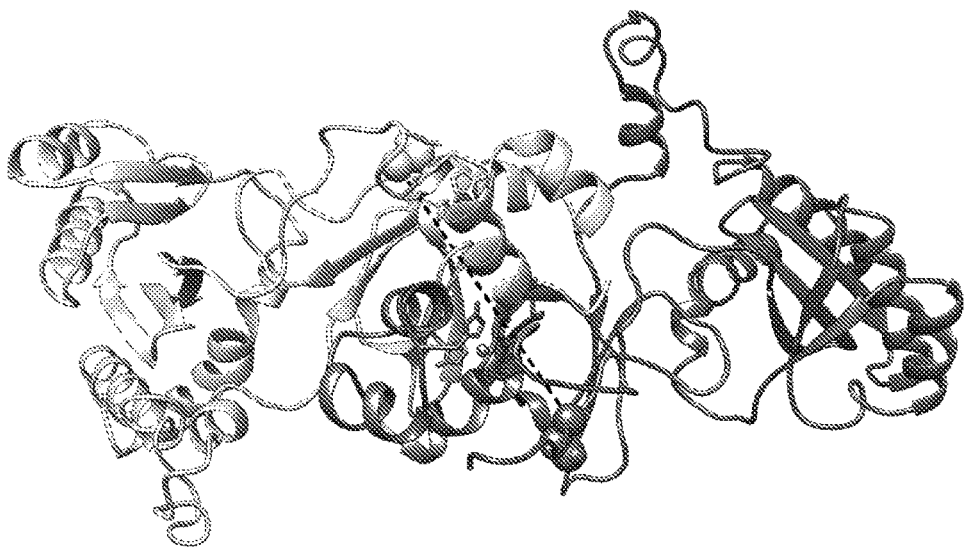

IN proteins are composed of three distinct structural domains (FIGS. 1A and B). The largest (amino acids 51-209 in human immunodeficiency virus (HIV) IN) is the central catalytic core domain (CCD or core). This domain contains the D,D(35)E motif of acidic residues that coordinate the required divalent metal ions, Mg+2 or Mn+2. The isolated human immunodeficiency virus (HIV) IN core domain forms a dimer in solution, and the 3 dimensional structure of the core from several retroviral IN proteins has been solved by X-ray crystallography of either the isolated domain or two-domain fragments that include the N (NTD) or C-terminal (CTD) domains. The same extensive interface of two core domains (e.g., FIG. 1A left Core Dimer) has been observed in every crystal structure analyzed so far and, consequently, it is believed to be physiologically relevant. The isolated, Zn+2-binding NTD (amino acids 1-50) and the SH3-like CTD (amino acids 210-286) of HIV IN also form dimers in solution. The spatial relationships between the CTDs and cores are different in each of the two-domain crystal structures that have been determined, and the crystal structure of the NTD+core, two-domain fragment shows a different NTD:NTD interface than that observed in the NMR structure of the NTD alone.

Full-length IN proteins are known to exist as monomers, dimers, and tetramers in solution, and complementation experiments indicate that IN functions as a multimer. An IN dimer appears to be the most catalytically active form for the endonucleolytic processing of a single-end viral DNA substrate in vitro. However, as two processed DNA ends must be joined by IN to host DNA in a concerted fashion in vivo, a tetramer is assumed to be the minimal functional multimer for this step. Purification and analysis of covalently cross-linked multimers of HIV-1 IN showed that although a dimer could process and join a single viral DNA end substrate, only a tetramer was capable of catalyzing the concerted integration of two viral ends into a target DNA (Faure, A et al. (2005) Nucleic Acids Res. 33(3), 977-986). Analyses of in vitro assembled HIV IN synaptic complexes containing viral and target DNA substrates, also indicate that concerted integration is catalyzed by an IN tetramer (Li, M et al. (2006) Embo J. 25(6), 1295-1304).

Models for IN dimers (FIG. 1A) and tetramers have been derived from consolidation of the crystal structures of two-domain protein fragments. However, experimental knowledge has been lacking concerning the disposition of the three domains with respect to each other, in the intact full-length monomer or multimers. The crystal structure of full-length IN from the human prototype foamy virus (PFV) was recently solved in complex with viral DNA (Hare, S et al. (2010) Nature 464, 232-236) revealing two different dimer interfaces for IN within the intasome structures.

Accordingly, the invention features methods for inhibiting the capability of retroviral integrase to insert or otherwise support or facilitate the insertion of retrovirus DNA into host cell DNA. In one aspect, a method for inhibiting the capability of a retrovirus to insert retrovirus DNA into host cell DNA comprises inhibiting the formation of multimers, preferably inhibiting the formation of functional multimers, and more preferably inhibiting the formation of a reaching dimer of a retroviral integrase protein in a host cell infected with the retrovirus. Inhibiting the formation of the reaching dimer may comprise inhibiting intermolecular interactions between amino acids in the C-terminal domain of a first retrovirus integrase monomer and amino acids in the C-terminal domain of a second retrovirus integrase monomer that mediate the formation of the reaching dimer, and/or inhibiting the intermolecular interactions between amino acids in the N-terminal domain of a first retrovirus integrase monomer and amino acids in the C-terminal domain of a second retrovirus integrase monomer that mediate the formation of the reaching dimer, and/or inhibiting the intermolecular interactions between amino acids in the N-terminal domain of a first retrovirus integrase monomer and amino acids in the N-terminal domain of a second retrovirus integrase monomer that mediate the formation of the reaching dimer.

Inhibiting the formation of multimers of a retroviral integrase protein may comprise contacting a host cell with an effective amount of a compound that inhibits the formation of multimers, including the reaching dimer of the retroviral integrase protein. The multimers may comprise any combination of multimers, and preferred multimers include dimers and tetramers.

A robust FRET based assay for IN reaching dimer formation was employed, using the HIV-1 Integrase (IN) protein that preferentially forms reaching dimers (2CS-F181T). The assay buffer conditions included the following: 25 mM HEPES (pH7.0), 20 mM MgSO4, 50 µM ZnSO4, 10% DMSO, 10% PEG 8 kDa, 1 mM DTT, and include 0.25 µM HIV-1-IN (2CS-F181T) labeled at C280 with a Cy3 donor, and 0.25 µM HIV-1-IN (2CS-F181T) labeled at C280 with Cy5 acceptor. Final buffer conditions include 180 mM NaCl and 15-30 mM urea from IN protein storage buffer. Reactions totaling 20 µl per well were made up in 384 plate format, incubated for 3 hrs and run at room temperature of 25'C. Standard untreated control wells were prepared with the above conditions, and experimental wells included the addition of 20 nl test compound in DMSO "pinned" in, resulting in a single concentration of compound at 10 µM. Negative control wells were as above but included 1M NaCl, while positive control wells had Heparin pinned in at a final concentration of 5 µg/ml. Blanks were as above but with no IN, buffer added in its place.

After all pinning was completed, plates were sealed, vortexed for 10 seconds, then centrifuged at 1000×g for 1 min. Plates were then left at room temperature of 25° C. for three hours incubation. Plates were then un-sealed and read on the Perkin-Elmer Envision plate reader equipped with filter sets for 685 and 590 wavelength measurements. Runs of 10 plates per day were performed to screen the entire Chemical Diversity set of 50,000 compounds obtained from ChemDiv, Ltd. A variety of statistical methods were compared for plate and run normalization, and ranking of hits for further validation.

Altogether, 320 hits were identified that either increased or decreased the FRET signal beyond 3 standard deviations; thus, an initial hit rate of 0.6% was observed. Validation of the 320 hits comprised a simple dose response assay (0.01, 0.1 and 1.0 uM compound) and confirmed hits were analyzed with multi-variate statistical ranking. 197 of the higher ranked compounds were then tested in a cross validation assay for inhibition of integrase catalytic activities of both single end joining and concerted integration at a compound concentration of 10 uM. This resulted in 20 hits that also inhibited catalysis of integration. These 20 cross-validated hits largely fall into three distinct scaffold classes with differential effects on IN catalytic function. The identification of these distinct classes adds legitimacy to the rationale of this approach to discover allosteric inhibitors of protein-protein interactions required for enzyme function. By following this method, general classes of chemical compounds were identified as capable of inhibiting HIV-1 integrase catalytic activity and, thus, capable of inhibiting the capability of a retrovirus to insert retrovirus DNA into a host DNA.

This disclosure provides such chemical compounds that have shown promise as inhibitors of multimer formation of the retroviral integrase protein and inhibition of infectivity in cultured cells, and thus, have implications for treatment of HIV. Accordingly, the invention features compounds (and/or pharmaceutically acceptable salts thereof), compositions, and methods for inhibiting the multimerization of the retroviral integrase protein, inhibiting infection, as well as methods for treating HIV. The methods may be carried out in vitro, ex vivo, in vivo, or in situ.

The final validated hits fall into a two scaffold classes with distinct differential effects on Integrase catalytic function. The first class of compounds below are dual inhibitors of single end joining and concerted integration. The second class of compounds below have the very interesting property of not inhibiting single end joining events, while specifically inhibiting concerted integration. We interpret this to mean that second class of compounds affect multimerization at a specific interface that is required for concerted activity. The identification of these different classes adds legitimacy to the rationale of this approach to discover allosteric inhibitors of protein-protein interactions required for enzyme function.

The first class of compounds (or pharmaceutically acceptable salt thereof) is referred to herein as toxoflavin derivatives and has the general chemical Formula I:

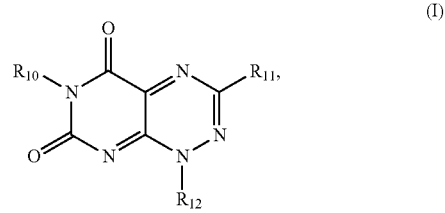

(I)

wherein $R_{10}$ and $R_{12}$ are each independently a H or a $C_1$-$C_3$ alkyl group;

$R_{11}$ is H, a $C_1$-$C_3$ alkyl group,

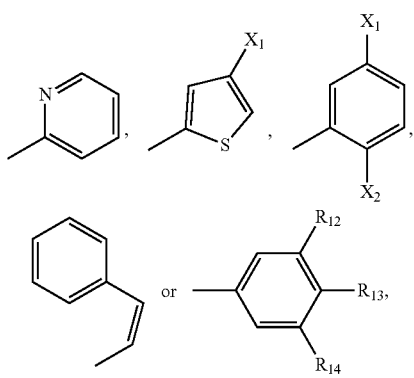

wherein each of $R_{12}$, $R_{13}$, and $R_{14}$ are independently selected from the group consisting of H, a $C_1$-$C_3$ alkyl group, $-NO_2$, halogen, $-CH_2F$, $-CHF_2$, and $-CF_3$, and wherein $X_1$ and $X_2$ are halogens and are either the same or different. Specific examples of compounds according to Formula I include those listed in the following Table 1.

TABLE 1

| Ref. | Relative % concerted integration (IC50) | Structure |
|---|---|---|
| I-1 (TF-1) | 3.84% (IC50 of 0.20 μM) | 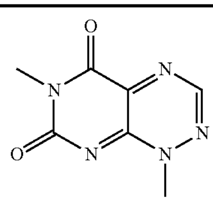 |
| I-2 | 6.33% | 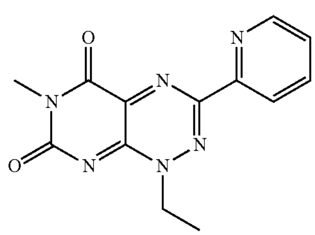 [SMILES: CCn1nc(-c2ccccn2)nc2c(=O)n(C)c(=O)nc1-2] |
| I-3 | 2.07% | 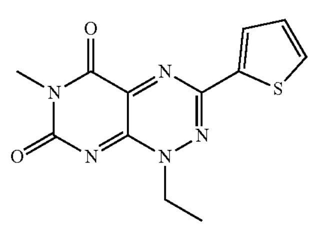 [SMILES: CCn1nc(-c2cccs2)nc2c(=O)n(C)c(=O)nc1-2] |
| I-4 | 0.26% | 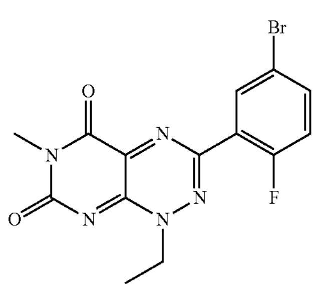 [SMILES: CCn1nc(-c2cc(Br)ccc2F)nc2c(=O)n(C)c(=O)nc1-2] |

TABLE 1-continued

| Ref. | Relative % concerted integration (IC50) | Structure |
|---|---|---|
| I-5 | 0.72% | 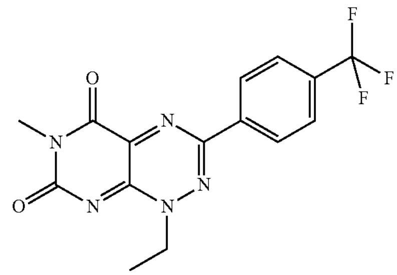 [SMILES: CCn1nc(-c2ccc(C(F)(F)F)cc2)nc2c(=O)n(C)c(=O)nc1-2] |
| I-6 | 1.72% | 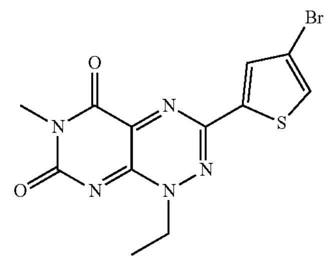 [SMILES: CCn1nc(-c2cc(Br)cs2)nc2c(=O)n(C)c(=O)nc1-2] |
| I-7 | 0.07% | 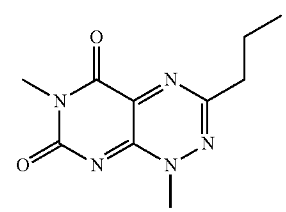 [SMILES: CCCc1nc2c(=O)n(C)c(=O)nc-2n(C)n1] |
| I-8 | 0.42% | 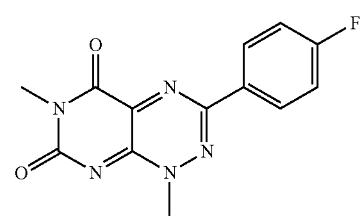 [SMILES: Cn1nc(-c2ccc(F)cc2)nc2c(=O)n(C)c(=O)nc1-2] |
| I-9 | 2.73% | 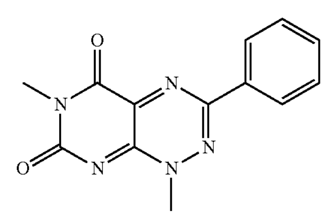 [SMILES: Cn1nc(-c2ccccc2)nc2c(=O)n(C)c(=O)nc1-2] |
| I-10 | 1.56% | 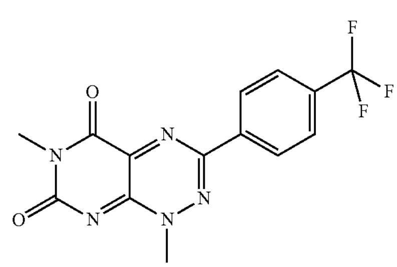 [SMILES: Cn1nc(-c2ccc(C(F)(F)F)cc2)nc2c(=O)n(C)c(=O)nc1-2] |

TABLE 1-continued

| Ref. | Relative % concerted integration (IC50) | Structure |
|---|---|---|
| I-11 | 1.76% | 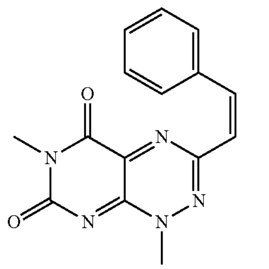 [SMILES: Cn1nc(/C=C\c2ccccc2)nc2c(=O)n(C)c(=O)nc1-2] |
| I-12 | 3.26% | 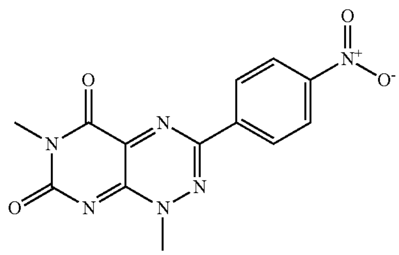 [SMILES: Cn1nc(-c2ccc([N+](=O)[O-])cc2)nc2c(=O)n(C)c(=O)nc1-2] |
| I-13 (TF-88) | 7.07% (IC50 of 0.27 μM) | 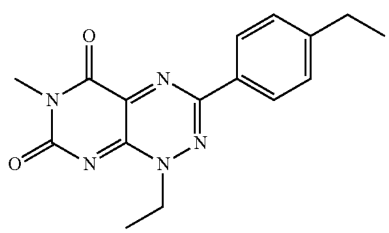 [SMILES: CCc1ccc(-c2nc3c(=O)n(C)c(=O)nc-3n(CC)n2)cc1] |

The second class of compounds (or pharmaceutically acceptable salt thereof) is referred to herein as NBF (Nitro-Benzo-Furazan) derivatives and has the general chemical Formula II:

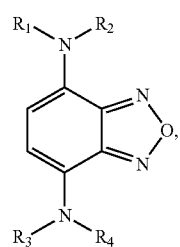

(II)

wherein
$R_1$, $R_2$, $R_3$, and $R_4$ are independently selected from
a hydrogen atom,
an aliphatic group having a carbon number of from 1 to 18 in which one or more hydrogen atoms may be substituted by a halogen atom,
an aliphatic group having a carbon number of from 2 to 18 which comprises at least one moiety selected from the group consisting of —O—, —S—, —C(=O)—, —C(=O)—O—, —C(=O)—S—, —C(=O)—NH—, —N-succinimidyl, and —O—C(=O)—NH—,
wherein at least one of the pairs $R_1$ and $R_2$ or $R_3$ and $R_4$ may be connected to form an alicyclic group, and wherein the aliphatic group optionally comprises at least one halogen atom. Specific examples of NBF derivative compounds according to Formula II include those listed in the following Table 2.

TABLE 2

| Ref. | Structure |
|---|---|
| II-1 | 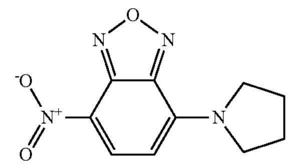 |
| II-2 (NBF-1) | 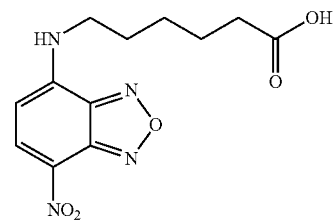 [SMILES: O=C(O)CCCCCNc1ccc([N+](=O)[O-])c2nonc12] |
| II-3 (NBF-2_ | 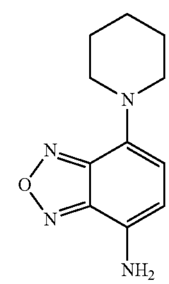 [SMILES: Nc1ccc(N2CCCCC2)c2nonc12] |
| II-4 (NBF-X) | 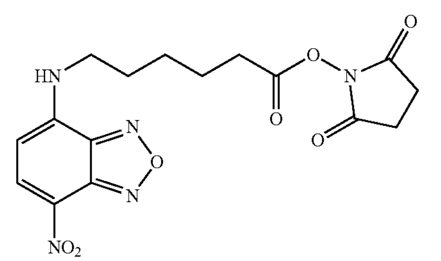 [SMILES: O=C(CCCCCNc1ccc([N+](=O)[O-])c2nonc12)ON1C(=O)CCC1=O] |

Pharmaceutically acceptable salts of any of the forementioned compounds may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise FDA-approved.

The compounds may be formulated as a composition, for example, with a carrier. Compositions may comprise a compound of Formula I-1, Formula I-2, Formula I-3, Formula I-4, Formula I-5, Formula I-6, Formula I-7, Formula I-8, Formula I-9, Formula I-10, Formula I-11, Formula I-12, Formula I-13, Formula II-1, Formula II-2, Formula II-3, Formula II-4 or a pharmaceutically acceptable salt thereof. The composition may include more than one, including any combination, of Formula I-1, Formula I-2, Formula I-3, Formula I-4, Formula I-5, Formula I-6, Formula I-7, Formula I-8, Formula I-9, Formula I-10, Formula I-11, Formula I-12, Formula I-13, Formula II-1, Formula II-2, Formula II-3, and Formula II-4. The composition may include other HIV-1 integrase inhibitors. The carrier is preferably a pharmaceutically acceptable carrier. Pharmaceutically acceptable carriers include aqueous vehicles such as water, alcohol (e.g., ethanol or glycol), saline solutions, dextrose solutions, and balanced salt solutions, as well as nonaqueous vehicles such as alcohols and oils, including plant or vegetable-derived oils such as olive oil, cottonseed oil, corn oil, canola oil, sesame oil, and other non-toxic oils. The compositions may comprise one or more pharmaceutically acceptable excipients.

The compositions preferably comprise an effective amount of the compound such as a compound having Formula I-1, Formula I-2, Formula I-3, Formula I-4, Formula I-5, Formula I-6, Formula I-7, Formula I-8, Formula I-9, Formula I-10, Formula I-11, Formula I-12, Formula I-13, Formula II-1, Formula II-2, Formula II-3, Formula II-4 or any combination thereof, or pharmaceutically acceptable salt of any of Formula I-1, Formula I-2, Formula I-3, Formula I-4, Formula I-5, Formula I-6, Formula I-7, Formula I-8, Formula I-9, Formula I-10, Formula I-11, Formula I-12, Formula I-13, Formula II-1, Formula II-2, Formula II-3, Formula II-4, or any combination thereof.

The compositions may be prepared to provide from about 0.05 mg to about 500 mg of the compound, or pharmaceutically acceptable salt thereof. The compositions may comprise from about 1 mg to about 200 mg of the compound, may comprise from about 10 mg to about 200 mg of the compound, may comprise from about 10 mg to about 100 mg of the compound, may comprise from about 50 mg to about 100 mg of the compound, may comprise from about 20 mg to about 400 mg of the compound, may comprise from about 100 mg to about 300 mg of the compound, and may comprise from about 50 mg to about 250 mg of the compound, or pharmaceutically acceptable salt thereof.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administrations. The compositions may be formulated in a suitable controlled-release vehicle, with an adjuvant, or as a depot formulation.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions.

Solid dosage forms include tablets, pills, powders, bulk powders, capsules, granules, and combinations thereof. Solid dosage forms may be prepared as compressed, chewable lozenges and tablets which may be enteric-coated, sugar coated or film-coated. Solid dosage forms may be hard or encased in soft gelatin, and granules and powders may be provided in non-effervescent or effervescent form. Solid dosage forms may be prepared for dissolution or suspension in a liquid or semi-liquid vehicle prior to administration. Solid dosage forms may be prepared for immediate release, controlled release, or any combination thereof. Controlled release includes, but is not limited to delayed release, sustained release, timed pulsatile release, and location-specific pulsatile release, and combinations thereof.

Liquid dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions may be oil-in water or water-in-oil emulsions.

Pharmaceutically acceptable excipients utilized in solid dosage forms include coatings, binders, lubricants, diluents, disintegrating agents, coloring agents, flavoring agents, preservatives, sweeteners, and wetting agents. Enteric-coated tablets, due to their enteric-coating, resist the action of stomach acid and dissolve or disintegrate in the neutral or alkaline intestines. Other examples of coatings include sugar coatings and polymer coatings. Sweetening agents are especially useful in the formation of chewable tablets and lozenges. Pharmaceutically acceptable excipients used in liquid dosage forms includes solvents, suspending agents, dispersing agents, emulsifying agents, surfactants, emollients, coloring agents, flavoring agents, preservatives, and sweeteners.

Non-limiting examples of binders include glucose solution, acacia mucilage, gelatin solution, sucrose and starch paste. Non-limiting examples of lubricants include talc, starch, magnesium or calcium stearate, lycopodium and stearic acid. Non-limiting examples of diluents include lactose, sucrose, starch, kaolin, salt, mannitol and dicalcium phosphate. Non-limiting examples of disintegrating agents include corn starch, potato starch, bentonite, methylcellulose, agar and carboxymethylcellulose. Non-limiting examples of emulsifying agents include gelatin, acacia, tragacanth, bentonite, and surfactants such as polyoxyethylene sorbitan monooleate. Non-limiting examples of suspending agents include sodium carboxymethylcellulose, pectin, tragacanth, veegum and acacia.

Non-limiting examples of coloring agents include any of the approved certified water soluble FD and C dyes, mixtures thereof, and water insoluble FD and D dyes suspended on alumina hydrate. Non-limiting examples of sweetening agents include dextrose, sucrose, fructose, lactose, mannitol and artificial sweetening agents such as saccharin, aspartame, sucralose, acelsulfame potassium, and other artificial sweeteners. Non-limiting examples of flavoring agents include synthetic flavors and natural flavors extracted from plants such as fruits and mints, and synthetic blends of compounds which produce a pleasant sensation. Non-limiting examples of wetting agents include propylene glycol monostearate, sorbitan monooleate, diethylene glycol monolaurate and polyoxyethylene laurel ether. Non-limiting examples of enteric-coatings include fatty acids, fats, waxes, shellac, ammoniated shellac and cellulose acetate phthalates. Non-limiting examples of film coatings include hydroxyethylcellulose, sodium carboxymethylcellulose, polyethylene glycol 4000 and cellulose acetate phthalate. Non-limiting examples of preservatives include glycerin, methyl and propylparaben, ethylparaben, butylparaben, isobutylparaben, isopropylparaben, benzylparaben, citrate, benzoic acid, sodium benzoate and alcohol.

Elixirs include clear, sweetened, hydroalcoholic preparations. Pharmaceutically acceptable carriers used in elixirs include solvents. Syrups include concentrated aqueous solutions of a sugar, for example, sucrose, and may contain a preservative. An emulsion is a two-phase system in which one liquid is dispersed throughout another liquid. Pharmaceutically acceptable carriers used in emulsions may include emulsifying agents and preservatives. Suspensions may use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Sources of carbon dioxide include sodium bicarbonate and sodium carbonate. Coloring and flavoring agents may be used in all such dosage forms.

Additional excipients that may be included in any dosage forms include, but are not limited to antimicrobial agents, isotonic agents, buffers, antioxidants, local anesthetic agents, sequestering or chelating agents, analgesic agents, antiemetic agents, and other agents to enhance selected characteristics of the formulation.

Antimicrobial agents may be cidal or static, and may be antimicrobial, antifungal, antiparasitic, or antiviral. Non-limiting examples of commonly used antimicrobial agents include phenols or cresols, mercurials, benzyl alcohol, chlorobutanol, methyl and propyl p-hydroxybenzoic acid esters, thimerosal, benzalkonium chloride and benzethonium chloride. Acidic or basic pH may be used for antimicrobial effects in some aspects. Non-limiting examples of isotonic agents include sodium chloride and dextrose. Non-limiting examples of buffers include phosphate and citrate buffers. A non-limiting example of a chelating agent for metal ions is EDTA.

The disclosure also features methods for inhibiting HIV-1 integrase multimerization. Such methods may comprise treatment methods, by which HIV-1 integrase multimerization inhibition treats patients with HIV since HIV-1 integrase multimerization and/or activation and/or biologic activity plays a role in this condition.

In some aspects, the methods comprise contacting HIV-1 integrase with an effective amount of a compound or composition comprising Formula I-1, Formula I-2, Formula I-3, Formula I-4, Formula I-5, Formula I-6, Formula I-7, Formula I-8, Formula I-9, Formula I-10, Formula I-11, Formula I-12, Formula I-13, Formula II-1, Formula II-2, Formula II-3, Formula II-4 or any combination thereof or any pharmaceutically acceptable salt thereof. The composition may comprise any dosage form and/or any excipients, including those described or exemplified herein.

The biologic activity of HIV-1 integrase is inhibited by the compounds or composition of this disclosure with less than about a 100 nM $IC_{50}$, more with less than about a 50 nM $IC_{50}$, more preferably with less than about a 40 nM $IC_{50}$, more preferably with less than about a 30 nM $IC_{50}$, more preferably with less than about a 20 nM $IC_{50}$, more preferably with less than about a 10 nM $IC_{50}$, more preferably with less than about a 8 nM $IC_{50}$, and more preferably with less than about a 5 nM $IC_{50}$.

In some aspects, the methods comprise contacting a cell expressing HIV-1 integrase with an effective amount of a compound or composition comprising Formula I-1, Formula I-2, Formula I-3, Formula I-4, Formula I-5, Formula I-6, Formula I-7, Formula I-8, Formula I-9, Formula I-10, Formula I-11, Formula I-12, Formula I-13, Formula II-1, Formula II-2, Formula II-3, Formula II-4 or any combination thereof or any pharmaceutically acceptable salt thereof. The composition may comprise any dosage form and/or any excipients, including those described or exemplified herein. In contacting the cell in this way, the compound or composition inhibits the biologic activity of HIV-1 integrase in the cell, preferably by disrupting the multimerization and subsequent catalytic activity at the integration step. The action of the compounds might also be to alter or inhibit productive IN multimers at other stages in the virus life cycle, and abrogate the IN functional role at other steps like RNA binding or reverse transcription. The cell may be any cell in which HIV-1 is expressed or is active. The cell may be a cell stably transformed with a nucleic acid encoding HIV1. The cell may be a cell line. The cell may be within the body of a subject.

Administration may be according to any technique or route suitable to the HIV patient's needs. Administration may be, for example, oral, parenteral, or via direct injection. Delivery may be via the bloodstream. Delivery may be passive.

Use of an HIV-1 integrase inhibitor according to Formula I-1, Formula I-2, Formula I-3, Formula I-4, Formula I-5, Formula I-6, Formula I-7, Formula I-8, Formula I-9, Formula I-10, Formula I-11, Formula I-12, Formula I-13, Formula II-1, Formula II-2, Formula II-3, Formula II-4 or a pharmaceutically acceptable salt thereof, or a composition thereof in the treatment of HIV are provided. The disclosure features use of an HIV-1 integrase inhibitor according to Formula I-1, Formula I-2, Formula I-3, Formula I-4, Formula I-5, Formula I-6, Formula I-7, Formula I-8, Formula I-9, Formula I-10, Formula I-11, Formula I-12, Formula I-13, Formula II-1, Formula II-2, Formula II-3, Formula II-4 or any combination thereof, or a pharmaceutically acceptable salt thereof, or a composition thereof in the treatment of HIV. Use may be in the manufacture of a medicament for HIV treatment as provided.

The following examples are provided to describe the invention in greater detail. They are intended to illustrate, not to limit, the invention.

EXAMPLES

Materials And Methods

Cross Validation Assay for Catalytic Activity and IC50 Determination

Assay for inhibition of catalytic activity and determination of the inhibitory concentration at 50% activity (IC50). Buffer conditions were as follows:

20 mM HEPES (7.0), 5 mM DTT, 10% PEG 8 KDa, 10% DMSO, 100 mM NaCl, 10 mM $MgCl_2$, 25 nM $ZnSO_4$, 1 uM HIV IN (Wild-type monomer), 0.5 uM IR 19/21 HIV U5 donor duplex DNA, 10 nM pBSK-Zeo circular plasmid target. The reaction volume is 10 ul, with an ionic strength 170 mM Na+ equivalent. Inhibitors were added in DMSO, with final concentrations in the 1 nM to 1 mM range. Catalytic assay reaction times were 2 hours at 37° C. Specific order of addition was as follows:

Buffer+IN+Mg+Zn were incubated for 5 minutes at 0° C.; then inhibitor added and incubated for 30 minutes at 0° C. Next donor DNA was added and incubated 15 minutes at 0° C. after which plasmid target was added and incubated 15 minutes at 0° C. Catalysis was begun by transferring to 37° C. and incubating for 2 hours. Reactions were stopped by making each reaction a final concentration of 25 mM EDTA, 0.5% SDS and 1 mg/ml Protease K, which removed protein in 30-60 min at 37° C. The samples were then run in a 1%, 1×TBE agarose gel to directly detect single and concerted integration bands using a Licor odyssey scanner.

Example 1

Determination of Inhibitor IC50

Figure 2:
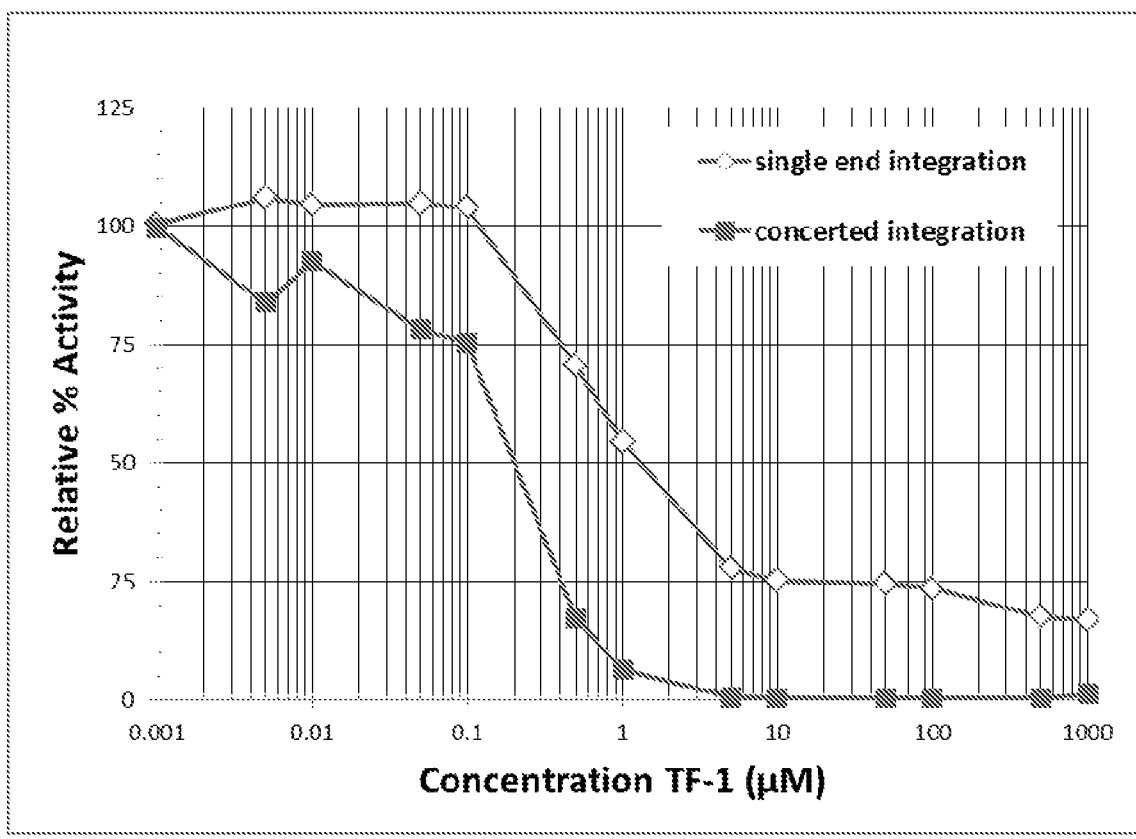
FIG. 2 shows the inhibition curve for the inhibitor I-1 (TF1).

FIG. 2 shows the inhibition curve for the inhibitor I-1 (TF1). To determine the IC50 for each of the validated compounds, the catalytic assay was performed as described above, and both single end (open diamonds) and concerted integration (closed squares) products were quantitated, and the relative percent activity was plotted as a function of the inhibitor concentration. The data in Tables 3 and 4 supports FIG. 2.

TABLE 3

| I.I. (K Counts) | I.I. (K Counts) - Blank | AVG POS I.I. cnts - BL | Rel % Activity |
|---|---|---|---|
| 5.469 | 0 | | |
| 138.397 | 132.928 | | |
| 140.069 | 134.6 | 136.285 | 100 |
| 146.797 | 141.328 | | |
| 142.49 | 137.021 | | 100.540 |
| 149.683 | 144.214 | | 105.818 |
| 147.859 | 142.39 | | 104.479 |
| 148.233 | 142.764 | | 104.754 |
| 146.91 | 141.441 | | 103.783 |
| 101.889 | 96.42 | | 70.749 |
| 79.722 | 74.253 | | 54.483 |
| 43.265 | 37.796 | | 27.733 |
| 39.794 | 34.325 | | 25.186 |
| 38.842 | 33.373 | | 24.488 |
| 37.581 | 32.112 | | 23.562 |
| 29.444 | 23.975 | | 17.592 |
| 28.523 | 23.054 | | 16.916 |

TABLE 4

| Name | uM | Form | I.I. (K Counts) | I.I. (K Counts)- Blank | AVG POS I.I. cnts-BL | Rel % Activity | I.I. (K Counts) CI/SI |
|---|---|---|---|---|---|---|---|
| Blank | 0 | F3 | 7.515 | 0 | | | |
| POS-1 | 0 | F3 | 204.711 | 197.196 | | | |
| POS-2 | 0 | F3 | 188.627 | 181.112 | 183.763 | 100 | 1.348 |
| POS-3 | 0 | F3 | 180.496 | 172.981 | | | |
| TF-1 | 0.001 | F3 | 190.541 | 183.026 | | 99.599 | 1.336 |
| TF-1 | 0.005 | F3 | 161.438 | 153.923 | | 83.762 | 1.067 |
| TF-1 | 0.01 | F3 | 177.328 | 169.813 | | 92.409 | 1.193 |
| TF-1 | 0.05 | F3 | 151.215 | 143.7 | | 78.199 | 1.007 |
| TF-1 | 0.1 | F3 | 145.798 | 138.283 | | 75.251 | 0.978 |
| TF-1 | 0.5 | F3 | 39.465 | 31.95 | | 17.387 | 0.331 |
| TF-1 | 1 | F3 | 19.303 | 11.788 | | 6.415 | 0.159 |
| TF-1 | 5 | F3 | 8.81 | 1.295 | | 0.705 | 0.034 |
| TF-1 | 10 | F3 | 8.285 | 0.77 | | 0.419 | 0.022 |
| TF-1 | 50 | F3 | 8.187 | 0.672 | | 0.366 | 0.020 |
| TF-1 | 100 | F3 | 8.348 | 0.833 | | 0.453 | 0.026 |
| TF-1 | 500 | F3 | 8.311 | 0.796 | | 0.433 | 0.033 |
| TF-1 | 1000 | F3 | 9.975 | 2.46 | | 1.339 | 0.107 |

Example 2

Labeling Binding Site

In order to determine which amino acid residues in integrase are proximal to the binding site for formula II class compounds, we took advantage of the N-succinimidyl group on the compound shown in formula II-4, which selectively forms a covalent bond with the primary amine in lysine side chains. Wildtype Integrase at 20 µM concentration was incubated with the 11-4 compound at a molar ratio of 1:1 (compound II-4:IN monomer) for 2 hours, after which labeled protein was quenched and separated from unbound compound by gel filtration. Labeled samples were then run on BisTris gradient SDS gels with antioxidants included, which were then stained and Integrase bands were sent for trypsinolysis and MS/MS detection of lysine containing peptides that had the expected mass gain for covalent compound binding. Peptide fragmentation analyses (y and b series ions) were also performed to determine which particular lysine was covalently modified.

Figure 3:
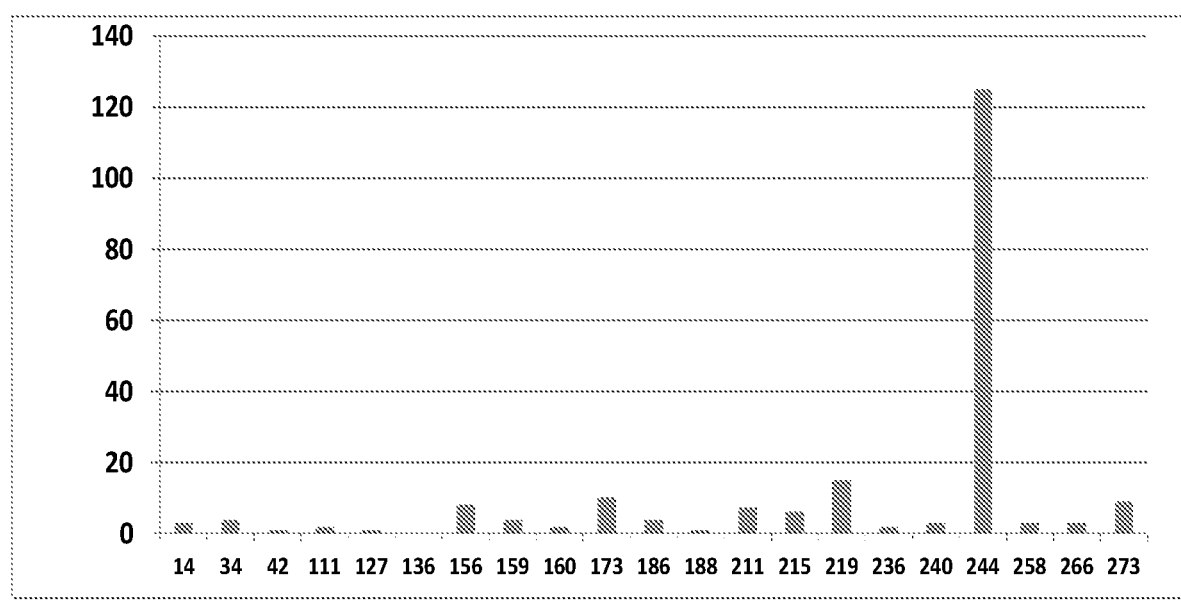
FIG. 3 is a graph showing the relationship of the mass spectral peptide count for compound II-4 labeled peptides versus each HIV integrase lysine position, according to the present invention.

FIG. 3 shows that the primary labeling site on the integrase protein is at K244, with some other lysines at greater than or equal to 10-fold lower levels.

Example 3

Inhibition Effects

Compounds were tested for inhibition of infectivity by treating target cells at the time of infection. Envelope pseudotyped virus particles were produced by transfection of 293T cells with a 4-plasmid system that generates virus capable of only a single round integration of a GFP reporter genome (Zufferey, R., et al. Self-inactivating lentivirus vector for safe and efficient in vivo gene delivery. J. Virol. 72, 9873-80 (1998)). Virus particles were isolated from filtered supernatants and used to infect HeLa cells that were incubated in the presence of the inhibitor compound for 1 hour prior to infection. Successful viral integration was scored as percent GFP positive cells at 48 hours post-infection. This assay was designed to test the inhibition of early steps in the retroviral life cycle up to and including integration of the provirus. These experiments were performed for a representative compound from each class I and II. Table 5 shows TF-1 inhibition of infectivity with an $EC_{50}$ (Effective Concentration) of 0.3 µM, which reveals a comparable concentration to its $IC_{50}$ for in vitro concerted integration. The class II NBF-X showed an $EC_{50}$ against infection of 5 µM (see the panel on right comparing both compounds to the known integrase active site inhibitor, Raltegravir).

TABLE 5

Toxicity compared to the $IC_{50}$ for single-end and concerted integration activity, and inhibition of infection.

| Name | Toxicity $LD_{50}$ (μM) | Single End $IC_{50}$ (μM) | Concerted $IC_{50}$ (μM) | Infectivity $EC_{50}$ (μM) | Tox/Infect $EC_{50}$ (μM) |
|---|---|---|---|---|---|
| TF-1 | 0.43 | 1.25 | 0.2 | 0.3 | >5 |
| TF-88 | 3.2 | 1.4 | 0.27 | ND | ND |
| NBF-1 | >50 | >1000 | 500 | ND | ND |
| NBF-2 | 25 | >1000 | 15 | ND | ND |
| NBF-X | >50 | 71 | 16 | 5 | >20 |
| RAL | >20 | 4.0 | 9.5 | 0.05 | >10 |

Figure 4:
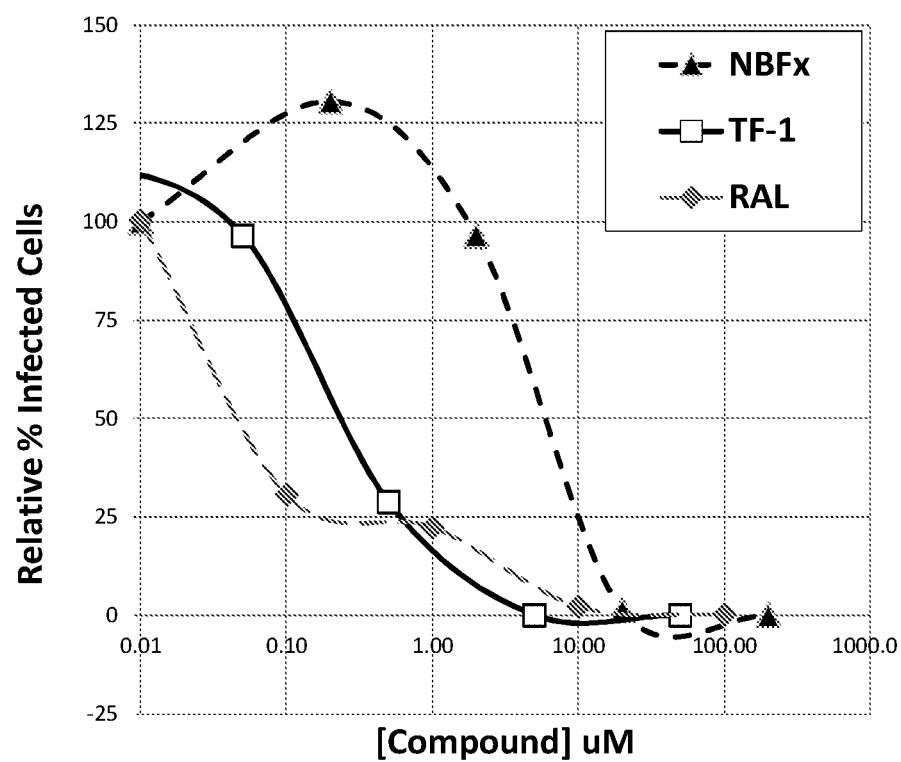
FIG. 4 is a graph showing the results that generated the infectivity column in Table 5.

Referring to Table 5, assay details are set forth above. Cellular toxicity experiments (left column) tested compound exposure for 3 days, and corresponding lethal dose ($LD_{50}$) were determined and compared to that required for inhibition of catalytic integration activities. Inhibition of catalytic activity assays are described above in the Materials And Methods section "Cross Validation assay for catalytic activity and IC50 determination." Inhibition of infection in cell culture is described in the text above, and $EC_{50}$ is the effective concentration of compound at which 50% maximal infection level occurs. The last column on the right (Tox/Infect) is a less rigorous measure of cell toxicity during the infection experiment with only 24 hours of exposure to compound. ND=Not Done; RAL positive control active site inhibitor Raltegravir. FIG. 4 shows the results that generated of the infectivity column in Table 5, and each data point represents the average of a triplicate assay.

The demonstration that two different compound scaffold classes first identified for their ability to inhibit reaching dimer formation, also show inhibition of catalysis in vitro, and most importantly inhibition of wildtype virus infection in cell based assays provides strong evidence for the biological importance of the reaching dimer. These results are early experimental support of the hypothesis that inhibiting such functional IN multimerization is a viable antiviral strategy with attractive therapeutic potential.

A few compounds from each scaffold class were tested for toxicity using cultured HeLa cells plated the day before compounds were tested at various dilutions. After a 3 day incubation period, cell viability was assessed using vital dyes which living cells convert to a fluorescent form for readout at 590 nm. Such fluorescence is proportional to the number of living cells remaining after the drug exposure. Preliminary lethal dose ($LD_{50}$) results for the compounds are also listed in Table 6, which compared toxicity results with the $IC_{50}$ for single-end and concerted integration, in vitro and inhibition of infection in vivo. TF-88 shows a 10-fold separation between inhibition of concerted integration and toxicity. NBF-X does not have apparent toxicity in the tested range up to 50 μM, and may also have a 10-fold window between inhibitory concentrations and toxicity concerns.

Example 4

Specificity

To determine the specificity of inhibition, these compounds were tested against other retroviral integrases for inhibition of both single end and concerted integration, in vitro. If class I or II scaffolds exerted their effects through a non-specific mechanism of action (i.e. redox cycling, or general reactivity and protein modification), they would be expected to inhibit all viral integrases equally. However, results show that neither TF-1 or NBF-X had inhibitory activity for the related retrovirus Prototype Foamy Virus (PFV) integrase single end or concerted integration catalysis (tested up to 1 mM and 0.35 mM concentration, respectively, see Table 6). Inhibitory activity against the Avian Sarcoma Virus integrase was detectable with NBF-X, but at concentrations approximately three times higher than for the HIV integrase. The observed specificity for class I and II inhibitors against HIV-1 integrase (as compared to the other two viral integrases) exceeds the specificity of the known active site inhibitor Raltegravir (RAL). As compounds from both scaffolds have marked specificity for the HIV-1 integrase, these results support the validity of our screening approach,

TABLE 6

| Name | HIV Single End $IC_{50}$ (μM) | HIV Concerted $IC_{50}$ (μM) | ASV Single End $IC_{50}$ (μM) | ASV Concerted $IC_{50}$ (μM) | PFV Single End $IC_{50}$ (μM) | PFV Concerted $IC_{50}$ (μM) |
|---|---|---|---|---|---|---|
| TF-1 | 1.25 | 0.2 | >100 | >100 | >1000 | >1000 |
| NBF-X | 65 | 16 | 175 | 53 | >350 | >390 |
| RAL | 4.0 | 9.5 | 22 | 0.6 | <10 | 1.0 |

The invention is not limited to the embodiments described and exemplified above, but is capable of variation and modification within the scope of the appended claims.

We claim:

1. A method for inhibiting HIV-1 integrase multimerization in a cell comprising HIV-1 integrase, the method comprising contacting HIV-1 integrase with an amount of a compound of Formula II effective to inhibit the biologic activity of HIV-1 integrase:

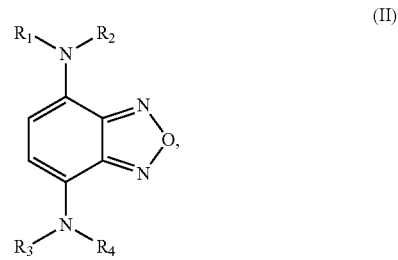

(II)

wherein
$R_1$, $R_2$, $R_3$, and $R_4$ are independently selected from
a hydrogen atom,
an aliphatic group having a carbon number of from 1 to 18 in which one or more hydrogen atoms may be substituted by a halogen atom,
an aliphatic group having a carbon number of from 2 to 18 which comprises at least one moiety selected from the group consisting of —O—, —S—, —C(=O)—, —C(=O)—O—, —C(=O)—S—, —C(=O)—NH—, N-succinimidyl, and —O—C(=O)—NH—, wherein at least one of the pairs $R_1$ and $R_2$ or $R_3$ and $R_4$ may be connected to form an alicyclic group, and wherein the aliphatic group optionally comprises at least one halogen atom.

2. The method of claim 1 wherein the compound is

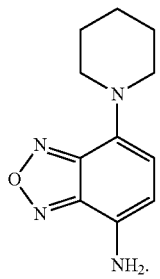 [SMILES: Nc1ccc(N2CCCCC2)c2nonc12]

3. The method of claim 1, wherein the compound is comprised in a composition comprising a pharmaceutically acceptable carrier.

4. The method of claim 1, wherein the method is carried out in vivo or in vitro.

5. A method for treating an HIV patient in need thereof, comprising administering to the patient an effective amount of an HIV-1 integrase multimerization inhibitor of Formula II,

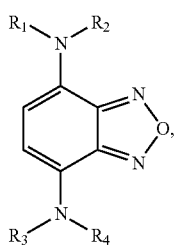

(II)

wherein $R_1$, $R_2$, $R_3$, and $R_4$ are independently selected from a hydrogen atom, an aliphatic group having a carbon number of from 1 to 18 in which one or more hydrogen atoms may be substituted by a halogen atom, an aliphatic group having a carbon number of from 2 to 18 which comprises at least one moiety selected from the group consisting of —O—, —S—, —C(=O)—, —C(=O)—O—, —C(=O)—S—, —C(=O)—NH—, N-succinimidyl, and —O—C(=O)—NH—, wherein at least one of the pairs $R_1$ and $R_2$ or $R_3$ and $R_4$ may be connected to form an alicyclic group, and wherein the aliphatic group optionally comprises at least one halogen atom.

6. The method of claim 5 wherein the compound is

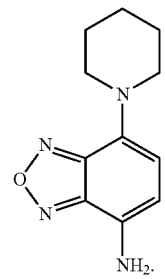

7. The method of claim 5, wherein the compound is comprised in a composition comprising a pharmaceutically acceptable carrier.

8. The method of claim 5, wherein the method is carried out in vivo or in vitro.

\* \* \* \* \*

UNITED STATES PATENT AND TRADEMARK OFFICE
CERTIFICATE OF CORRECTION

| | |
|---|---|
| PATENT NO. | : 10,888,564 B2 |
| APPLICATION NO. | : 16/480624 |
| DATED | : January 12, 2021 |
| INVENTOR(S) | : Mark D. Andrake et al. |

It is certified that error appears in the above-identified patent and that said Letters Patent is hereby corrected as shown below:

In the Specification

In the STATEMENT OF GOVERNMENT SUPPORT Section, Column 1, Lines 17-20, delete the existing paragraph "The inventions described herein were made, in part, with funds obtained from the National Institutes of Health, Grant Nos. AI-040385 and AI-118589. The U.S. government may have certain rights in these inventions." and insert therefore -- This invention was made with government support under AI040385, and AI118589 awarded by the National Institutes of Health. The government has certain rights in the invention. --

Signed and Sealed this
Fifth Day of September, 2023

Katherine Kelly Vidal
*Director of the United States Patent and Trademark Office*